(12) United States Patent
Cavazza

(10) Patent No.: US 6,346,282 B1
(45) Date of Patent: Feb. 12, 2002

(54) NEUROPROTECTIVE COMPOSITION FOR THE PREVENTION AND/OR TREATMENT OF NERVOUS AND BEHAVIOURAL ALTERATIONS DUE TO ANXIETY STATES OR DEPRESSION, COMPRISING ACETYL-L-CARNITINE AND HYPERICIN

(75) Inventor: Claudio Cavazza, Rome (IT)

(73) Assignee: Sigma-Tau Healthscience S.p.A., Pomezia (IT)

( * ) Notice: Subject to any disclaimer, the term of this patent is extended or adjusted under 35 U.S.C. 154(b) by 0 days.

(21) Appl. No.: 09/719,551

(22) PCT Filed: Jun. 17, 1999

(86) PCT No.: PCT/IT99/00175

§ 371 Date: Dec. 26, 2000

§ 102(e) Date: Dec. 26, 2000

(87) PCT Pub. No.: WO99/66914

PCT Pub. Date: Dec. 29, 1999

(30) Foreign Application Priority Data

Jun. 25, 1998 (IT) ...................................... RMM98 0425

(51) Int. Cl.$^7$ ...................... A61K 35/78; A61K 31/205; A61K 31/12
(52) U.S. Cl. ...................... 424/730; 514/556; 514/680
(58) Field of Search ...................... 424/730; 514/680, 514/556

(56) References Cited

U.S. PATENT DOCUMENTS 5,911,992 A * 6/1999 Braswell et al.

* cited by examiner

*Primary Examiner*—William R. A. Jarvis
(74) *Attorney, Agent, or Firm*—Oblon, Spivak, McClelland, Maier & Neustadt, P.C.

(57) ABSTRACT

This invention relates to a composition of acetyl-L-carnitine in combination with hypericin and/or Hypericum extract (*Hypericum perforatum L.* (St. John's Wort)) in synergistically effective amounts. The composition is effective at treating a nervous alteration due to an anxiety state, irritability, or depression.

13 Claims, No Drawings

NEUROPROTECTIVE COMPOSITION FOR THE PREVENTION AND/OR TREATMENT OF NERVOUS AND BEHAVIOURAL ALTERATIONS DUE TO ANXIETY STATES OR DEPRESSION, COMPRISING ACETYL-L-CARNITINE AND HYPERICIN

This application is a 371 of PCT/IT99/00175, filed Jun. 17,1999

The present invention relates to a composition for the prevention and/or treatment of nervous and behavioural alterations due to anxiety states or depression.

Accordingly the composition may take the form and exert the action of a dietary supplement or of an actual medicine, depending upon the support or preventive action, or the strictly therapeutic action, which the composition is intended to exert in relation to the particular individuals it is to be used in.

Particularly the present invention relates to a composition which comprises in combination:

(a) acetyl L-carnitine or a pharmacologically acceptable salt thereof, optionally in combination with at least another "carnitine" where for "carnitine" is intended L-carnitine or an alkanoyl L-carnitine selected from the group comprising propionyl-L-carnitine, valeryl L-carnitine, isovaleryl L-carnitine or their pharmacologically acceptable salts; and (b) 1,3,4,6,8,13-hexahydroxy-10,11-dimethylphenanthro[1,10,9,8-opqra]perylene-7,14-dione (hypericin) or Hypericum extract (*Hypericum perforatum L.*, "Saint-John's-wort") comprising at least 0.3% by weight of hypericin.

The new composition can be orally, parenterally, rectally or transdermally administered both to humans and animals, as a pharmaceutical composition, dietary supplement or phytotherapy preparation.

The use of Hypericum extracts was already well known to popular medicine owing to its ability to combat a series of pathological alterations including both conditions such as depression, anxiety, insomnia, neuralgia, migraine, dyspepsia and sciatica, and inflammatory and scarring processes.

Hypericum contains numerous active components in its extracts, the most interesting of which are the naphthodianthrones, flavonoids, phloroglucinols, xanthones and a number of essential oils.

The main naphthodianthrones are hypericin, pseudohypericin and emodinanthrone.

The main flavonoids are proanthocyanidins consisting in various trimers and tetramers or polymers of catechin and epicatechin.

The phloroglucinols include prenylated derivatives of phloroglucinol, hyperpherin and perforin.

In addition to caffeic acid, coumaric acid and ferulic acid, essential oils are also present, consisting mainly in monoterpenes and sesquiterpenes.

Of all the components, hypericin is the one which more than any other has proved most interesting owing to its easy characterisation and its specificity of action.

It is, in fact, mainly to hypericin that the acknowledged anti-depressant, anxiolytic, scar-healing and antiviral effects of Hypericum extracts are to be attributed.

Recent research has demonstrated that hypericin inhibits monoamino-oxidases and cerebral serotinin reuptake, and reduces the expression of cytokines, particularly interleukin-6.

Many types of activity are exerted by the carnitines, which are generally capable of activating the processes necessary for ATP synthesis via β-oxidation of fatty acids as well as of promoting stabilisation of the cell membranes against oxidative processes of both the cardiovascular and cerebral systems.

Acetyl L-carnitine improves behavioural parameters in the rat and electro-encephalographic abnormalities in elderly patients.

Neuroregeneration can also be improved by the administration of carnitines.

Surprisingly, it has now been demonstrated that a composition containing as its characterising components a combination of:

(a) acetyl L-carnitine or a phamacologically acceptable salt therof; and (b) hypericin, is extremely effective in the prevention and/or therapeutic treatment of nervous disorders related to states of anxiety or depression, as a result of the potent synergistic effect produced by its components.

It has also been found that, advantageously, component (a) may further comprise a "carnitine" selected from the group consisting of L-carnitine, propionyl L-carnitine, valeryl L-carnitine, isovaleryl L-carnitine or their pharmacologically acceptable salts or mixtures thereof, and that component (b) may consist of a hypericum (*Hypericum perforatum L.*, "Saint-John's-wort") extract containing at least 0.3% by weight of hypericin.

The (a):(b) weight-to-weight ratio ranges from 1:0.01 to 1:1. When component (b) of the composition is present in the form of an extract of vegetable products containing it, these vegetable products include the flowers, buds and apical leaves of the Hypericum plant.

TOXICOLOGY TESTS

In these tests, the administration of high doses of either the carnitine mixture, or of acetyl L-carnitine, or of the Hypericum extract or hypericin alone or of a combination of the aforesaid components proved to be well tolerated both after single-dose administration and after prolonged administration for thirty days. Tests conducted both in rats and mice, with the oral administration of doses of 2 g/kg of carnitine mixture (consisting of a combination of L-carnitine+acetyl L-carnitine+propionyl L-carnitine+isovaleryl L-carnitine present in the same weight ratio to one another), or of 2 g/kg of acetyl L-carnitine, or 1 g/kg of Hypericum extract containing approximately 0.3% of hypericin, or of 3 mg/kg of hypericin, or various combinations of these products, i.e. 1 g/kg of carnitine mixture or 1 g/kg of acetyl L-carnitine in combination with 600 mg/kg of Hypericum extract or 1 mg/kg of hypericin, have provided evidence of a lack of toxic effects or mortality in the animals thus treated. Even the prolonged administration for thirty days consecutively of doses of 500 mg/kg of carnitine mixture or of acetyl L-carnitine in combination with 500 mg/kg of Hypericum extract or 1 mg/kg of hypericin, was well tolerated and devoid of toxic effects. At the end of this treatment, no abnormal blood chemistry parameters were detectable and the histology examination performed on the main organs (heart, lungs, liver, kidneys) failed to reveal any damaging effects of the combination of products administered.

Protective action against abnormal brain serotonin concentrations induced by neurotoxic substances Since changes in concentration of cerebral biogenic amines regulate both excitatory and depressive emotional behaviour states, it was decided, in view of the above-mentioned action of hypericin and Hypericum extracts at catecholamine and particularly serotoninergic receptor level and on the reuptake of serotonin itself, to evaluate changes in cerebral concentrations of serotonin after treatment with Hypericum extracts, hypericin, carnitine mixture or acetyl L-carnitine, alone or in various combinations, in conjunction with treatment with a substance such as fenfluramine, the neurotoxicity of which manifests itself also through a reduction in brain serotonin concentrations. It is well known, in fact, that fenfluramine [N-ethyl-α-methyl-m-(trifluoromethyl)phenethylamine] exerts a neurotoxic action on the brain, which is identifiable both histologically on the basis of derangement of the cerebral serotoninergic structures and through depletion of serotonin concentrations in the brain.

The tests were conducted using a group of (Sprague-Dawley) male rats which were administered fenfluramine orally at the dose of 5 mg/kg twice daily for 5 days consecutively, either alone or at the same time, and for the same period, as a carnitine mixture (400 mg/kg) (consisting in a combination of L-carnitine+acetyl L-carnitine+propionyl L-carnitine+isovaleryl L-carnitine present in the same weight ratio to one another), or acetyl L-carnitine (400 mg/kg), or Hypericum extract (with a 0.3% hypericin content–300 mg/kg), or hypericin (1 mg/kg), or various combinations of these products at the same doses.

Two weeks after treatment, the animals were sacrificed and the cerebral cortex isolated and subjected to measurement of the cerebral content both of serotonin (5-HT) and of hydroxy-indole-acetic acid (5-HIAA) according to the method described by Wise (Wise, C. D., *Anal. Biochem.*, 18, 94, 1967) and modified by Ricaurte (Ricaurte, G. A., *J. Pharmacol. Exptl. Ther.*, 261, 616, 1992).

The results obtained in these tests (Table 1) demonstrate that fenfluramine, as a result of its neurotoxic activity, causes substantial lowering of brain concentrations both of 5-HT and 5-HIAA. The reduction in serotonin concentrations is then countered by the administration of Hypericum extract or hypericin, and this effect becomes much more marked, leading almost to abolition of the effect of fenfluramine, when the Hypericum extract or hypericin are combined with the carnitine mixture or with acetyl L-carnitine. Whereas the positive effect of Hypericum extract and of hypericin on serotonin reuptake was well known, no such activity was known for the carnitines, and thus these tests demonstrate a potent synergistic protective effect at the neuronal level and on serotonin concentrations reduced by a neurotoxic substance such as fenfluramine.

TABLE 1

Concentrations of serotonin (5-HT) and of hydroxy-indole-acetic acid (5-HIAA) in the brain in rats treated with fenfluramine together with a carnitine mixture or with acetyl L-carnitine, Hypericum extract, hypericin, or various combinations of these products

| | Cerebral (cortex) concentrations (ng/mg tissue) | |
|---|---|---|
| Treatment | 5-HT | 5-HIAA |
| CO | 0.37 ± 0.018 | 0.28 ± 0.015 |
| FE | 0.17 ± 0.010 | 0.14 ± 0.011 |
| CC | 0.36 ± 0.023 | 0.30 ± 0.009 |
| AC | 0.35 ± 0.020 | 0.28 ± 0.012 |
| HE | 0.38 ± 0.026 | 0.30 ± 0.029 |
| HYP | 0.36 ± 0.019 | 0.30 ± 0.030 |
| CC + FE | 0.20 ± 0.015 | 0.16 ± 0.009 |
| AC + FE | 0.18 ± 0.011 | 0.15 ± 0.019 |
| HE + FE | 0.26 ± 0.023 | 0.24 ± 0.021 |
| HYP + FE | 0.28 ± 0.020 | 0.25 ± 0.018 |
| CC + HE + FE | 0.36 ± 0.029 | 0.25 ± 0.023 |
| CC + HYP + FE | 0.38 ± 0.025 | 0.29 ± 0.025 |
| AC + HE + FE | 0.36 ± 0.024 | 0.26 ± 0.016 |
| AC + HYP + FE | 0.39 ± 0.029 | 0.28 ± 0.028 |

CO = controls
FE = fenfluramine
CC = carnitine mixture
AC = acetyl L-carnitine
HE = Hypericum extract
HYP = hypercin Tests of exploratory activity in mice (Hole Board Test)

It has been proved that in animals, and particularly in the mouse, that small doses of amphetamine can cause a state of anxiety with a corresponding reduction in motor exploration activity. This reduction is not related to sedation caused by the drug in the animal and can be offset using anxiolytic agents.

Using the technique described by Boissier (Boissier J. R., *Physiol. Behav.*, 2. 447. 1967), tests (Hole Board Test) were conducted in order in a group of mice to ascertain whether the reduction in motor exploration activity induced in the animals by low-dose amphetamine (1 mg/kg i.p.) could be corrected by the oral administration of a carnitine mixture (consisting of a combination of L-carnitine+acetyl L-carnitine+propionyl L-carnitine+isovaleryl L carnitine in the same weight ratio to one another), or of acetyl L-carnitine, or Hypericum extract, or hypericin, or various combinations of these products. As can be seen from the data in Table 2, whereas the administration of carnitines alone had no effect on the exploratory activity of the animals, the administration of Hypericum extracts and of hypericin almost restored exploratory activity to normal, and the combination of carnitines plus Hypericum extract or hypericin increased exploratory activity, to an extent similar to the effect of the higher amphetamine dose.

TABLE 2

Motor exploration activity in the mouse (Hole Board Test) 30 minutes after administration of amphetamine (1 and 5 mg/kg i.p.) together with carnitine mixture, acetyl L-carnitine, Hypericum extract, hypericin, or various combinations of these products.

| Treatment | | Variations compared to controls |
|---|---|---|
| — | Amphetamine 1 mg/kg | −45 |
| — | Amphetamine 5 mg/kg | +55 |
| CC | Amphetamine 1 mg/kg | −50 |
| AC | Amphetamine 1 mg/kg | −48 |
| HE | Amphetamine 1 mg/kg | −10 |
| HYP | Amphetamine 1 mg/kg | −5 |
| CG + HE | Amphetamine 1 mg/kg | +15 |
| CG + HYP | Amphetamine 1 mg/kg | +19 |
| AG + HE | Amphetamine 1 mg/kg | +25 |
| AG + HYP | Amphetamine 1 mg/kg | +20 |

CC = carnitine mixture 400 mg/kg
AC = acetyl L-carnitine 400 mg/kg
HE = Hypericum extract 300 mg/kg
HYP = hypericin 1 mg/kg Platform Test Another behavioural test in the mouse is the Platform Test described by Burnell (Burnell, J. A., *J. Comp. Physiol. Psychol.*, 1, 147, 1965) which consists in placing the animals on a wooden platform at various heights from the ground and counting the number of animals that do not hesitate to get down from the platform. Ten animals were used per group and the percentage of animals that managed to descend from the platform was calculated. As can be seen from the results in Table 3, whereas none of the control animals descended from the platform at the height of 9 cm from the ground and only approximately 50% descended from the 5-cm platform, the animals' behaviour was modified by the administration of Hypericum extract (300 mg/kg) or hypericin (1 mg/kg). It was modified even more by the administration of a combination of these products plus the carnitine mixture (L-carnitine+acetyl L-carnitine+propionyl L-carnitine+isovaleryl L-carnitine present in the same weight ratio to one another, making a total dose of 400 mg/kg) or acetyl L-carnitine 400 mg/kg, neither of which modifies the animals' behaviour when administered alone.

The results of these tests also clearly show a distinct potentiation of the action of Hypericum extract (300 mg/kg) and hypericin (1 mg/kg) as a result of combination with carnitines.

TABLE 3

Platform Test in mice

| | % of mice descending from | |
|---|---|---|
| Treatment | 9 cm | 5 cm |
| Controls | 0 | 60 |
| Carnitine mixture, 400 mg/kg | 0 | 70 |
| Acetyl L-carnitine, 400 mg/kg | 0 | 70 |
| Hypericum extract, 300 mg/kg | 20 | 90 |
| Hypericin, 1 mg/kg | 30 | 90 |
| Carnitine mixture, 400 mg/kg + Hypericum extract, 300 mg/kg | 70 | 100 |
| Carnitine mixture, 400 mg/kg + hypericin, 1 mg/kg | 60 | 100 |
| Acetyl L-carnitine, 400 mg/kg + Hypericum extract, 300 mg/kg | 60 | 100 |
| Acetyl L-carnitine, 400 mg/kg + hypericin, 1 mg/kg | 80 | 100 |

Tests of immobility induced by forced swimming

One of the tests regarded as being most significant for assessing the activity of antidepressant substances is the forced swimming test in the mouse, which measures the changes in swimming-induced immobility which the various test substances produce (Borsini, F., *Psychopharmacology*, 94, 147, 1988). In these tests, the technique described by Persolt was adopted (Persolt, R. D., *Eur. J. Pharmacol.*, 57, 201, 1979—Persolt, R. D., *Arch. Int. Pharmacology*, 229, 327, 1977) using ten rats per group. The animals were placed in beakers measuring 14 cm in height and approximately 12 cm in internal diameter which were filled with water (20–22° C.) up to 7.5 cm from the rim and then left there for six minutes. The duration of the immobility was calculated during the last four minutes. The mice were considered immobile when they performed only the movements necessary to keep themselves afloat on the water.

The substances tested were administered orally in two administrations six hours and three hours prior to the start of the experiment.

As apparent from the results in Table 4, the period of immobility was reduced by the administration of Hypericum extract and hypericin, but the reduction was much more marked when Hypericum extract or hypericin were combined with the administration of the carnitine mixture (combination of L-carnitine+acetyl L-carnitine+propionyl L-carnitine+isovaleryl L-carnitine present in the same weight ratio to one another) or with acetyl L-carnitine, which, when administered alone, had no reducing effect on immobility time.

TABLE 4

Tests of immobility time induced by forced swimming in mice

| Treatment | Immobility time |
|---|---|
| Controls | 210 ± 8 |
| Carnitine mixture | 220 ± 7 |
| Acetyl L-carnitine | 204 ± 8 |
| Hypericum extract | 190 ± 9 |
| Hypericin | 195 ± 5 |
| Carnitine mixture + Hypericum extract | 170 ± 6 |
| Carnitine mixture + hypericin | 165 ± 4 |
| Acetyl L-carnitine + Hypericum mixture | 178 ± 9 |
| Acetyl L-carnitine + hypericin | 172 ± 7 |

The method adopted for these tests was the Scott method (Scott, J. P., *Physiol. Zool.*, 24, 273, 1951) as modified by Sanchez (Sanchez, C., *Psychopharmacology*, 110, 53. 1993). This method consists in making the mice aggressive by keeping them isolated for twenty-one days in a cage and in assessing, after treatment, the latency time needed to trigger the aggression of the isolated animal when another animal is put in the cage with it. Only animals with latency times of less than 10 seconds before attacking were included in the tests, and the time of attack was taken as the time the isolated animal bit or tried to bite the other animal introduced into the cage.

The observation time was 180 seconds and the experiment was started 30 minutes after administration of the products tested. All isolated animals were treated, both eight hours and half an hour before the test, with carnitine mixture (consisting of a combination of L-carnitine+acetyl L-carnitine+propionyl L-carnitine+isovaleryl L-carnitine in an equiponderal ratio to one another) (400 mg/kg), or with acetyl L-carnitine (400 mg/kg) or with Hypericum extract (300 mg/kg) or with hypericin (1 mg/kg), or with various combinations of these products.

The results of these tests (Table 5) demonstrate that, whereas carnitines alone do not modify aggression latency times in mice treated with them, their use in combination with either Hypericum extract or hypericin potentiates to a highly significant extent the reduction in aggression which the latter produce in mice.

These tests, too, demonstrate that an unexpected, sudden synergistic effect occurs between carnitines and Hypericum extract or hypericin.

TABLE 5

Isolation-induced aggression tests. Latency time of attack in male mice treated with carnitine mixture, acetyl L-carnitine, Hypericum extract, hypericin, or various combinations of these products.

| Treatment | Latency time in seconds |
| --- | --- |
| Controls | 8 ± 2 |
| Carnitine mixture, 400 mg/kg | 11 ± 1 |
| Acetyl L-carnitine, 400 mg/kg | 14 ± 3 |
| Hypericum extract, 300 mg/kg | 80 ± 10 |
| Hypericin, 1 mg/kg | 100 ± 9 |
| Carnitine mixture, 400 mg/kg + Hypericum extract, 300 mg/kg | 140 ± 12 |
| Carnitine mixture, 400 mg/kg + hypericin, 1 mg/kg | 150 ± 6 |
| Acetyl L-carnitine, 400 mg/kg + Hypericum extract, 300 mg/kg | 150 ± 9 |
| Acetyl L-carnitine, 400 mg/kg + hypericin, 1 mg/kg | 160 ± 11 |

Illustrative, non-limiting examples of formulations according to the invention are reported hereinbelow.

| | |
| --- | --- |
| 1) Carnitine mixture | mg 600 |
| (L-carnitine mg 150, acetyl L-carnitine mg 150, propionyl L-carnitine mg 150, isovaleryl L-carnitine mg 150) | |
| Hypericum extract (titled 0.3% of Hypericin) | mg 600 |
| 2) Carnitine mixture | mg 600 |
| (L-carnitine mg 150, acetyl L-carnitine mg 150, propionyl L-carnitine mg 150, isovaleryl L-carnitine mg 150) | |
| Hypericin | mg 2 |
| 3) Acetyl L-carnitine | mg 600 |
| Hypericum extract (titled 0.3% of Hypericin) | mg 600 |
| 4) Acetyl L-carnitine | mg 600 |
| Hypericin | mg 2 |
| 5) Carnitine mixture | mg 300 |
| (L-carnitine mg 75, acetyl L-carnitine mg 75, propionyl L-carnitine mg 75, isovaleryl L-carnitine mg 75) | |
| Hypericum extract (titled 0.3% of Hypericin) | mg 300 |
| 6) Carnitine mixture | mg 300 |
| (L-carnitine mg 75, acetyl L-carnitine mg 75, propionyl L-carnitine mg 75, isovaleryl L-carnitine mg 75) | |
| Hypericin | mg 1 |
| 7) Acetyl L-carnitine | mg 300 |
| Hypericum extract (titled 0.3% of Hypericin) | mg 300 |
| 8) Acetyl L-carnitine | mg 300 |
| Hypericin | mg 1 |
| 9) Carnitine mixture | mg 300 |
| (L-carnitine mg 75, acetyl L-carnitine mg 75, propionyl L-carnitine mg 75, isovaleryl L-carnitine mg 75) | |
| Hypericum extract (titled 0.3% of Hypericin) | mg 300 |
| L-tyrosine | mg 50 |
| Histidine | mg 50 |
| Taurine | mg 50 |
| Glutamine | mg 50 |
| Valine | mg 50 |
| Tryptophan | mg 50 |
| 10) Carnitine mixture | mg 300 |
| (L-carnitine mg 75, acetyl L-carnitine mg 75, propionyl L-carnitine mg 75, isovaleryl L-carnitine mg 75) | |
| Hypericum extract (titled 0.3% of Hypericin) | mg 300 |
| Phosphoserine | mg 100 |
| Glyceryl phosphorylcholine | mg 100 |
| Tryptophan | mg 100 |
| Tyrosine | mg 100 |
| COQ10 | mg 10 |
| Selenium | mg 10 |

What is meant by pharmacologically acceptable salt of L-carnitine or alkanoyl L-carnitine is any salt of these active ingredients with an acid that does not give rise to unwanted toxic or side effects. These acids are well known to pharmacy experts.

Non-limiting examples of suitable salts are the following: chloride; bromide; iodide; aspartate, acid aspartate; citrate, acid citrate; tartrate; phosphate, acid phosphate; fumarate; acid fumarate; glycerophosphate; glucose phosphate; lactate; maleate, acid maleate; orotate; oxalate, acid oxalate; sulphate, acid sulphate, trichloroacetate, trifluoroacetate and methane sulphonate.

A list of FDA-approved pharmacologically acceptable salts is given in *Int. J. of Pharm.* 33, (1986), 201–217; this latter publication is incorporated herein by reference.

The composition according to the invention may also comprise vitamins, coenzymes, minerals substances and antioxidants.

Appropriate excipients to be used to prepare the compositions having regards to the specific route of administration, will be apparent to the pharmacy and food industry experts.

I claim:

1. A composition, comprising:
   (a) a synergistically effective amount of acetyl-L-carnitine or a pharmacologically acceptable salt thereof; and
   (b) a synergistically effective amount of hypericin or Hypericum extract (*Hypericum perforatum L.*) comprising at least 0.3% by weight of hypericin.

2. The composition of claim 1, wherein ingredient (a) further comprises a carnitine selected from the group consisting of L-carnitine, propionyl L-carnitine, valeryl L-carnitine, isovaleryl L-carnitine a pharmacologically acceptable salt of L-carnitine, a pharmacologically acceptable salt of propionyl L-carnitine, a pharmacologically acceptable salt of valeryl L-carnitine, a pharmacologically acceptable salt of isovaleryl L-carnitine, and a mixture thereof.

3. The composition of claims 1 or 2, wherein the weight ratio of (a):(b) is from 1:0.01 to 1:1.

4. The composition of claim 1, wherein ingredient (b) is in the form of a vegetal extract which contains the ingredient itself.

5. The composition of claim 4, wherein said vegetal extract comprises a flower, a terminal bud or a leave of a Hypericum plant.

6. The composition of claim 1, wherein the pharmacologically acceptable salt of L-carnitine or alkanoyl L-carnitine is selected from the group consisting of chloride, bromide, iodide, aspartate, acid aspartate, citrate, acid citrate, tartrate, phosphate, acid phosphate, fumarate, acid fumarate, glycerophosphate, glucose phosphate, lactate, maleate, acid maleate, orotate, acid oxalate, sulphate, acid sulphate, trichloroacetate, trifluoroacetate methane sulphonate and a mixture thereof.

7. The composition of claim 1, which further comprises a vitamin, a coenzyme, a mineral substance, an antioxidant and a mixture thereof.

8. The composition of claim 1, orally administrable in the form of a dietary supplement.

9. The composition of claim 1, orally, parenterally, rectally or transdermally administrable dosage form.

10. The composition of claims 8 or 9, in a solid, semi-solid or liquid form.

11. The composition of claim 10 in the form of a pill, a tablet, a capsule, a granulate or syrup.

12. A method for the prevention of a nervous alteration due to an anxiety state, irritability or depression, comprising:
    administering the composition of claim 8 to a subject in need thereof.

13. A method for the therapeutic treatment of a nervous alteration due to an anxiety state, irritability or depression, comprising:
    administering the composition of claim 9 to a subject in need thereof.

* * * * *

UNITED STATES PATENT AND TRADEMARK OFFICE
CERTIFICATE OF CORRECTION

PATENT NO.    : 6,346,282 B1
DATED         : February 12, 2002
INVENTOR(S)   : Cavazza It is certified that error appears in the above-identified patent and that said Letters Patent is hereby corrected as shown below:

<u>Title page,</u>
Item [30], the Foreign Application Priority information should read:

-- [30]      Foreign Application Priority Data
      Jun. 25, 1998   (IT) ............................... RM98A000425 --

Signed and Sealed this

Seventeenth Day of September, 2002

*Attest:*

*Attesting Officer*

JAMES E. ROGAN
*Director of the United States Patent and Trademark Office*